Figure 1:
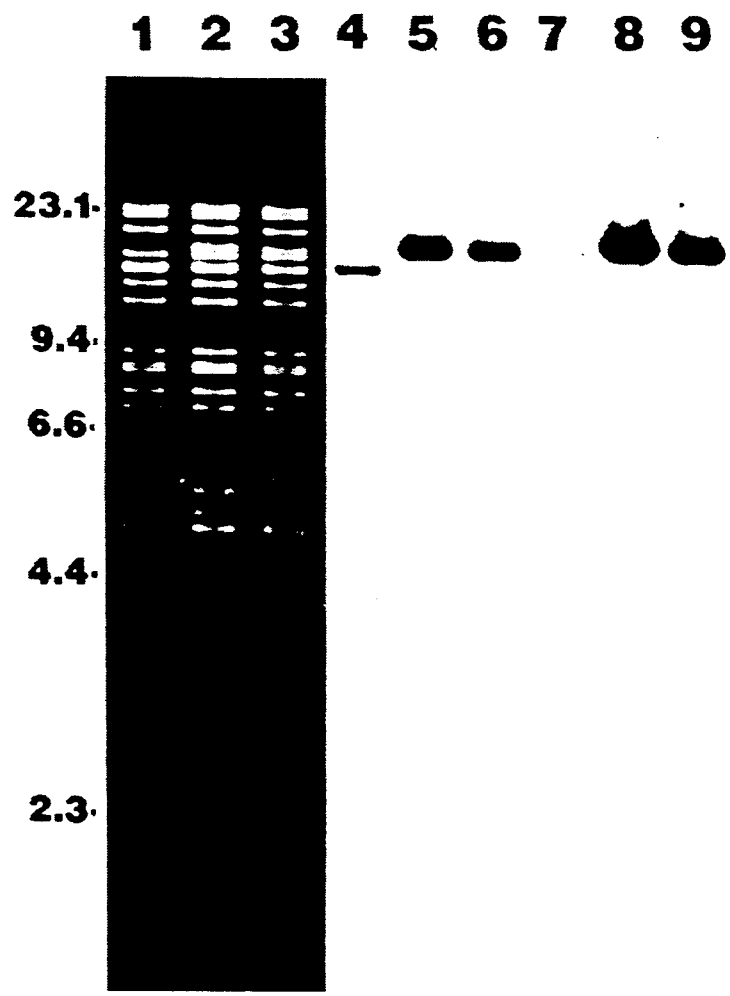
Figures 2A, 2B:
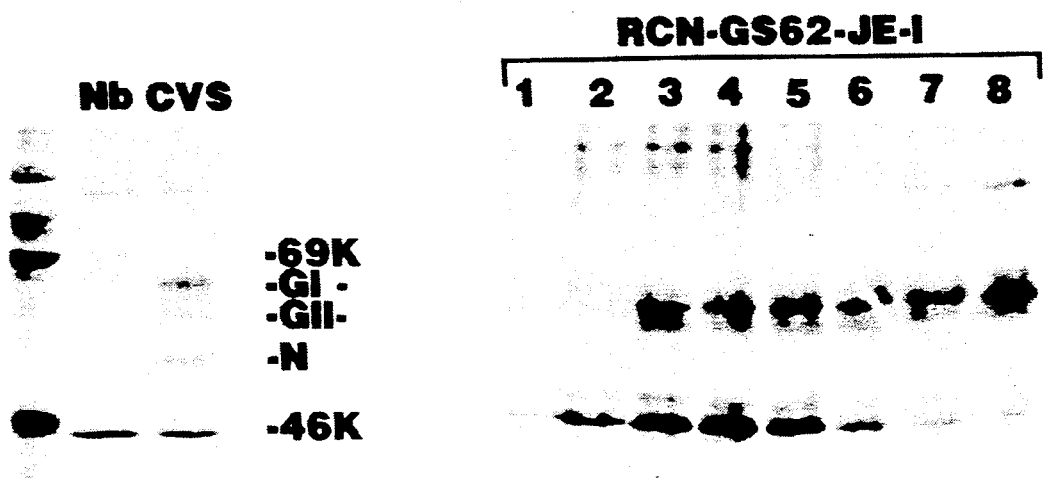
Figure 2C:
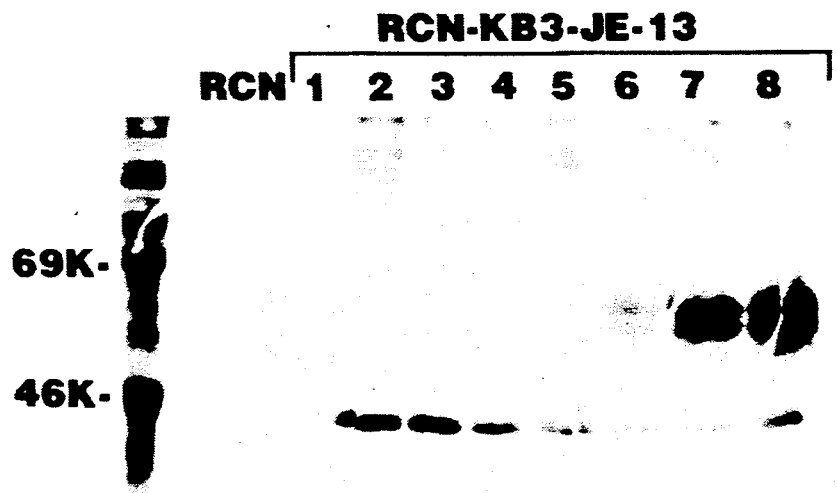

United States Patent [19]

Esposito et al.

[11] Patent Number: 5,266,313

[45] Date of Patent: Nov. 30, 1993

[54] RACCOON POXVIRUS AS A GENE EXPRESSION AND VACCINE VECTOR FOR GENES OF RABIES VIRUS AND OTHER ORGANISMS

[75] Inventors: Joseph J. Esposito; George M. Baer, both of Atlanta, Ga.

[73] Assignee: The United States of America as represented by the Department of Health and Human Services, Washington, D.C.

[21] Appl. No.: 829,597

[22] Filed: Feb. 3, 1992

Related U.S. Application Data

[63] Continuation of Ser. No. 198,213, May 25, 1988, abandoned, which is a continuation-in-part of Ser. No. 10,424, Feb. 3, 1987, abandoned.

[51] Int. Cl.$^5$ .............................................. A61K 39/12
[52] U.S. Cl. .......................................... 424/89; 435/5; 435/235.1; 935/65
[58] Field of Search ................. 435/235.1, 172.3, 948, 435/5; 424/89; 935/65

[56] References Cited

PUBLICATIONS

Esposito et al, Vaccines 89, Cold Spring Harbor Laboratory 1989, pp. 403–408.
The American Society for Virology 1991 Annual Meeting, Colorado State University, Fort Collins, Colo., Jul. 7–11, 1991, Workshop #63.
Baer, et al, *American Journal of Epidemiology* 93:487–490 1971.
*World Health Organization Technical Report Series* 709:57–62, 1984.
Wiktor, et al., *Proc. Natl. Acad. Sci. USA* 81:7194–7198, 1984.
Kieny, et al., *Nature* 312:163–166, 1984.
E. Krag Andersen *Proc. Symposium or Smallpox*, 53–64, 1969.
Gezondheidstraad, et al. *Symp. Series Immunobiol.* 19:235–242, 1972.
Yaye F. Hermans, *Bacteriological Proceedings* V12, p. 117, 1964.
Alexander, et al., *Journal of Wildlife Diseases* 8:119–126, 1972.
Esposito, et al., *Virology* 143:230–251, 1985.
Esposito, et al., *Virus Genes* 1:1,7–21, 1987.
Mackett, et al., *DNA Cloning* 2:191–211, 1985.
Smith, et al., *Laboratory Techniques in Rabies Appendix 5* pp. 354–357 1973.
Thomas, et al., *Archives of Virology* 49:217–227, 1975.
Parsons, et al., *Virology* 161:45–53, 1987.
Rosel, et al., *Journal of Virology*, 60:436–449, 1986.
Weir, et al., *Journal of Virology* 61:75–80, 1987.
Cochran, et al., *Journal of Virology*, 54:30–37, 1985.

*Primary Examiner*—Esther L. Kepplinger
*Assistant Examiner*—Donna C. Wortman
*Attorney, Agent, or Firm*—Birch, Stewart, Kolash & Birch

[57] ABSTRACT

Raccoon poxvirus, an organism that may be indigenous in nature, is established as a suitable substrate for insertion and expression of nucleotide coding sequence of heterolgous organisms. Two infectious raccoon poxvirus recombinants for expressing rabies virus surface spike glycoprotein (G) were produced by homologous recombination between raccoon poxvirus DNA and chimeric plasmids previously used for production of vaccinia virus recombinants by thymidine kinase insertional inactivation. Raccoons that were fed polyurethane baits loaded with raccoon poxvirus recombinant quickly developed high levels of rabies virus neutralizing antibodies and were protected when challenged with an otherwise lethal dose of raccoon rabies street virus. Dogs developed rabies virus neutralizing antibodies after feeding a vectored raccoon poxvirus recombinant in contrast to feeding a vaccinia: G recombinant that induced no rabies neutralizing antibodies. Cotton rats, skunks, mice and rabbits that were fed recombinant raccoon poxvirus developed variable levels of rabies neutralizing antibodies. All vaccinated cotton rats were protected from otherwise lethal rabies challenge.

10 Claims, 2 Drawing Sheets

RACCOON POXVIRUS AS A GENE EXPRESSION AND VACCINE VECTOR FOR GENES OF RABIES VIRUS AND OTHER ORGANISMS

This application is a continuation of application Ser. No. 07/198,213 filed on May 25, 1988, now abandoned, which is a continuation in part of co-pending U.S. patent application Ser. No. 07/010,424 filed Feb. 3, 1987 and now abandoned.

BACKGROUND OF THE INVENTION

1. Technical Field

The present invention is related to rabies vaccines More particularly, the present invention is related to a rabies vaccine provided by the establishment of a host organism as a substrate for inserting and expressing genetic information of other organisms.

2. State of the Art

Raccoon pox virus (RCN) was first isolated from upper respiratory tissues of two apparently healthy raccoons captured in 1961-62. The raccoons were captured during a survey of local wildlife at Aberdeen Proving Grounds, Maryland. This was reported by Herman, Y.F Bacteriol. Proc., 64th Ann. Meet. Amer. Soc. Microbiol. 1964 page 117, and Alexander. A.D. et al., J. Wildlife Dis. 1972:8:119-126. No gross lesions were seen during necropsy of the two raccoons. The sera of 22 of 92 raccoons from the same area showed raccoon poxvirus hemagglutinating-inhibiting (III) antibodies. This indicated the presence of the virus in nature at that time. The current distribution of RCN virus in nature is unknown. The biological characteristics of one isolate, including its DNA restriction map and its pathological innocuity when inoculated into raccoons, has been described by Thomas E.K. et al., Arch. Virol. 1975:49:217-227; Esposito J.J. & Knight J.C. Virology 1985:143:230-251; and Parsons B.L. & Pickup D.J. Virology 1987:161:45-53. In an earlier study by Esposito, J J. & Knight, J.C. Virology 1985:143:230-251 it was observed that thyymidine kinase (TK) nucleotide sequences within the DNA fragment Hind3-J of vaccinia virus cross hybridized with raccoon poxvirus DNA fragment Hind3-E. Chimeric plasmids like those designed for inserting rabies virus surface spike glycopiotein (G protein) coding sequences into the vaccinia virus TK region were reported by Esposito et al., Virus Genes 1987:1:7-22 and Esposito, J.J. Brechling, K. Moss, B. Patent Application No. 07/010,424, filed on Mar. 25, 1987.

In the United States, the wildlife species most involved in rabies transmission are skunks, raccoons, foxes, and insectivorous bats. Raccoons currently rank second to skunks as the major reservoir. Rabid foxes are a major source of the disease in Canada and many European countries. With the discontinued use of poisoning and trapping in the 1960s, attempts have been made to protect foxes from rabies via bait-delivered oral vaccination. The immunization of foxes by the feeding of live-attenuated rabies virus vaccine in sausages is disclosed by Baer, G.M. et al, Am. J Epidemiol. 1971:93:487-490 and the corresponding U.S Pat. No. 4,014,991. This form of immunization led to efficacy and safety studies of live-attenuated rabies vaccine in chicken head baits as described in the World Health Organization Expert Committee on Rabies 7th Report, 1984 Technical Report Series 709, WHO, Geneva. The virtual elimination of rabies in Switzerland and field trials in West Germany and other countries have indicated that oral-bait rabies vaccines can significantly curtail the spread of rabies. Although live-attenuated rabies virus vaccines are effective in immunizing foxes against rabies, they are not effective for immunizing skunks and raccoons.

A live recombinant vaccinia virus has been developed that expressed the G protein of rabies virus strain ERA and that induced rabies virus-neutralizing antibodies and protection against a rabies challenge. This is disclosed in the articles Wiktor, T.J. et al., PNAS 1984:81:7194-7198 and Kieny, M.P. et al., Nature 1984:312:163-166. The ERA-G recombinant vaccinia virus has been inoculated to vaccinate various animals against rabies, including bovines, or by feeding the recombinant to foxes and raccoons. The possibility that a recombinant vaccinia virus might be introduced into nature, however, has raised controversy largely because of the rare side effects in people that are associated with primary smallpox vaccination with vaccinia virus. Furthermore, the vaccinia: ERA-G recombinant uses vaccinia virus Copenhagen, a strain that has been associated with relatively increased side effect rates in humans when used during mass vaccinations against smallpox and increased virulence for laboratory animals as described by E. Krag-Anderson in Proceedings of Sypmposium on Smallpox 1969, pp. 53-64, B. Gusic, editor, Yugoslave Academy of Sciences and Arts, Zagreb, 1969 and by M.F. Polak in Symposium Series in Immunobiological Standardization: R.H. 1973:19:235-242 Regamy and H. Cohen, editors, S. Karger Publishing, Basel.

In order to overcome problems associated with use of relatively invasive strains of vaccinia virus like strain Copenhagen, six different chimeric plasmids for regulating different levels of expression of G protein of the CVS strain of rabies virus have been produced and disclosed by Esposito et al. Virus Genes 1987:1:7-22. These plasmids are for inserting nucleotide coding sequences of G protein into the viral TK locus of the New York Board of Health (NYBH) strain of vaccinia virus. This strain demonstrated relatively low side effect rates in people during mass vaccination programs. In the six different recombinants that were produced, vaccinia virus promoter $P_{7.5}$ which is an early/late class promoter or $P_{11}$ which is a late class promoter were used to drive expression of G protein. As described by Esposito et al., Virus Genes 1987:1:7-22, each of the six recombinants administered by intradermal scarification or by footpad injection protected mice against rabies challenge. One recombinant that was injected intramuscularly into five dogs provided protection against a lethal rabies challenge.

The industry is lacking a raccoon poxvirus as a substrate for inserting genes to provide a useful expression system. The known systems do not provide a recombinant raccoon poxvirus for expression of heterologous DNA such as rabies virus surface glycoprotein or recombinants such as raccoon poxvirus: rabies-G that can be produced by using chimeric plasmids, such as those with viral thymidine kinase flanking sequences and promoter sequences designed for production of vaccinia virus recombinant. The industry further lacks live raccoon poxvirus: rabies virus recombinants that can be administered as an oral bait-delivered vaccine to (1) protect raccoons and other wildlife species against rabies and (2) produce related immune-reagents and/or other types of veterinary vaccines.

SUMMARY OF THE INVENTION

The invention is a recombinant virus. The invention includes a recombinant raccoon poxvirus as a host organism. The raccoon poxvirus has a nucleotide coding sequence of a second organism. The nucleotide coding sequence is desirably a segment of a rabies virus nucleotide coding sequence.

The invention includes a pharmaceutical composition such as vaccine derived from the recombinant virus.

The invention includes a method for inducing protective immunity against rabies and a kit for detecting the presence of rabies.

BRIEF DESCRIPTION OF THE DRAWINGS

FIG. 1 depicts a resolution of thymidine kinase nucleotide coding sequences within standard raccoon poxvirus and raccoon poxvirus recombinants, and of rabies virus G protein encoding nucleotide sequences within recombinants.

FIG. 2 A, B, C depicts synthesis of G protein forms GI and GII as detected by radioimmunoprecipitation assay of raccoon poxvirus recombinant-infected cell cultures.

DETAILED DESCRIPTION OF THE INVENTION

The invention is a recombinant raccoon poxvirus. Such recombinant viruses can be used for the production of oral or injectable vaccines for wildlife, livestock, or companion animals to control rabies and for the production of related biochemical and immunobiological reagents. Raccoon poxvirus and vaccinia virus belong to same genus of Orthopoxvirus and have genetic homology. For this reason, raccoon poxvirus derived chimeric plasmids and many chimeric plasmids for inserting genes into vaccinia virus can be used interchangeably to produce vectored recombinants. Raccoon poxvirus has unique biological properties and appears to be indigenous in nature. This allows raccoon poxviruses to have uses and applications similar to other live vectored poxviruses including vaccinia, a smallpox vaccine virus that is not indigenous in nature.

The invention is described by reference to two desirable embodiment, recombinant virus RCN-KB3-JE-13 (RAB-G? or RCN-GS62-JE-I. The RCN-KB3-JE-13 (RAB-G) embodiment represents the preferred embodiment of the invention. This embodiment of the invention has been deposited into the American Type Culture Collection, Rockville, Maryland under Accession Number VR2212 on May 23, 1988. Upon request, the Commissioner of Patents shall have access to the deposit which shall be viably maintained for a period of 30 years or 5 years after the last request, or the life of the patent, whichever is longer. And upon issuance of a patent, the recombinants shall be made available to the public in accordance with the law and with appropriate restrictions and guidelines applicable to the safe handling and use of this class of infectious virus.

For the purpose of this invention, the following definitions are provided. A late promoter is defined as a DNA segment that includes nucleotide sequences that. regulate gene expression and are functionally active after, but not before, the replication of virus DNA in infected cells. An early/late promoter is defined as a DNA segment that includes nucleotide sequences that regulate gene expression and are functionally active before and after the replication of virus DNA. This temporal activity can be contiguous on or separable into subsets of the nucleotide sequences. Examples of late genes and early/late genes are described by Rosel et al., J. Virol. 1986:60:436–439, Weir & Moss J. Virol. 1987:61:75–80, and Cochran et al., J.Virol. 1985:54:30–37. Generally such promoters reside immediately upstream of nucleotide coding sequences for viral proteins. The above three documents and the documents cited below are hereby incorporated by reference.

The construction of a recombinant virus according to this invention involves selecting a strain of raccoon poxvirus. An acceptable raccoon poxvirus can include one of the two virus isolates from Aberdeen Proving Grounds, Maryland as disclosed by Herman, Y.F. Bacteriol. Proc., 64th Ann. Meet. Amer. Soc. Microbiol., 1964, page 117; Alexander, A.D. et al., J. wildlife Dis. 1972:8:119:126; Thomas E.K. et al., Arch Virol. 1975:49:217–227; Esposito J.J. & Knight J.C. Virology 1985:143:230–251; and Parsons B.L. & Pickup D.J. Virology 1987:161:45–53. The preferred embodiment of the invention utilizes thrice plaque-purified in CV1 cells, RCN virus isolate designated as V71-I-85A by the Centers for Disease Control (CDC), Poxvirus Laboratory, Atlanta, Georgia 30333. The DNA restriction electropherogram profile and map of this isolate has been described by Esposito J.J. & Knight J.C. Virology 1985:143:230–251 and Parsons B.L. Pickup D.J. Virology 1987:161:45–53. Another desirable isolate is designated V71-I-84 at the CDC and is also designated as ATCC VR-838 in the general repository catalog of The American Type Culture Collection, Rockville, Maryland 20852. This isolate has a similar, but not identical, DNA restriction endonuclease electropherogram profile compared to V71-I-85A and is characterized biologically by Thomas E.K. et al., Arch. Virol. 1975:49:217–227.

Insertion into the genome of RCN virus of nucleotide coding sequences for G protein is done by TK gene insertional inactivation using standard DNA recombination methodology that is well known in the art and described by Mackett et al., In "DNA Cloning: A Practical Approach" D.M. Glover, Ed., 1985, 2:191–211, IRL Press, Washington, D.C. More particularly, the methods described below for producing RCN recombinants with the chimeric plasmids pGS62-JE-I (early/late promoter type), and the pKB3-JE-13 (late promoter type) are essentially the same as those for producing NYBH vaccinia virus recombinants as disclosed by Esposito et al., Virus Genes 1987:1:7–22.

FIG. 1 shows resolution of TK coding sequences within RCN virus and recombinants, and detection of insertion therein in recombinants of rabies virus nucleotide coding sequences for G protein. Recombinant RCN viruses were produced by TK gene insertional inactivation using the same marker rescue and recombinant selection methods detailed before with NYBH vaccinia virus and the described chimeric plasmids pGS62-JE-I (early/late promoter type) and pKB3-JE-13 (late promoter type). In FIG. 1 Hind3 cleavage fragments are shown of virion DNA from thrice plaque-purified RCN virus (lanes 1, 4, 7), from recombinant virus RCN-GS62-JE-I (lanes 2, 5, 8), and from recombinant virus RCN-KB3-JE-13 (lanes 3, 6, 9) resolved by agarose gel electrophoresis (lanes 1–3), then blotted bidirectionally onto nitrocellulose sheets. One sheet (lanes 4–6) was probed by hybridization with a NYBH vaccinia virus TK segment, a Sau3A 0.888 kbp DNA fragment. The other sheet (lanes 7-9) was probed with G-cDNA. Migration positions of Lambda phage molecular weight marker DNA Hind3 fragments are also shown.

The ability to select in culture medium containing bromodeoxyuridine for TK-inactivated vectored recombinants and the hybridizations in FIG. 1 demonstrate that the location of inserted rabies virus G cDNA coding sequences is within the TK homologous sequence region of RCN virus. Comparison of electropherograms (lanes 1–3) of endonuclease cleaved DNA of standard RCN virus and recombinant RCN viruses, designated herein as RCN-GS62-JE-I and RCN-KB3-JE-13, show the DNA molecular weight increase that took place in RCN virus DNA fragment Hind3-E (13.5 kilobase pairs (kbp)). After recombination with G-cDNA, a new fragment appeared, Hind3-D in the recombinants (RCN-GS62-JE-I fragment Hind3-D=15.45 kbp; RCN-KB3-JE-13 fragment Hind3-D=15.35 kbp). Autoradiograms of the three virus DNAs (lanes 4-6) hybridized with the vaccinia virus TK cDNA resolve a single fragment of each virus, the aforementioned DNA fragments. Rabies virus G-cDNA, however, hybridized only with the Hind3-D fragment of the two recombinant viruses.

FIG. 2 shows synthesis of G protein forms GI and GII detected by radioimmunoprecipitation assay of RCN recombinant virus-infected cell cultures. At 8 hours' postinfection (hpi) for RCN virus (panel C) or at the times indicated for recombinants RCN-GS62-JE-I (panel B) and RCN-KB3-JE-13 (panel C), CV1 monkey kidney cell monolayers (multiplicity of infection=30 plaque-forming units (PFUs) purified virus per cell) were washed thrice with methionine-free culture medium, then pulse-labelled for 15 minutes at 370° C. with medium that contained $^{35}$S-methionine (100 uCi/ml). CVS rabies virus-infected (10 PFUs/cell) or mock-infected mouse neuroblastoma (Nb) cell monolayers (panel A) at 20 hpi were pulse-labelled similarly for 4 hours. Clarified cell extracts were incubated first with rabbit antiserum prepared against detergent (NP-40) extracted CVS rabies virus G protein (antiserum shows some nucleoprotein (N) reactivity) and then with protein-A (*S. aureus* fixed bacteria). Proteins were eluted from the bacteria and resolved on SDS-polyacrylamide gels (12%) and autoradiographed. Migration of molecular weight marker proteins (K represents $M_r$=1000) are also shown.

The radioimmunoprecipitations revealed that forms GI (67 kilodaltons (kDa)) and GII (62 kDa) that are found in CVS rabies virus infected cells comigrated with GI and GII forms that are expressed in cell monolayers separately infected with the RCN recombinant viruses. Moreover, the time that G protein first appears in recombinant virus-infected cells correlated with the expected time of activity of vaccinia virus promoter $P_{7.5}$, 1 to 2 hours' postinfection (hpi), and of $P_{11}$, 4 to 5 hours hpi. Further, an estimated tenfold higher concentration of G protein was detected in cells infected with RCN-KB3-JE-13 virus ($P_{11}$ driving G expression) compared with those infected with RCN-GS62-JE-I virus. Both RCN recombinants apparently directed faithful expression of G protein.

It is clear from the results illustrated in FIG. 1 that RCN virus accepts vaccinia expression cassettes that are flanked by vaccinia TK nucleotide sequences to target recombination. It is also noted that rabies virus G protein expressed in cell cultures via RCN virus is authentic because of its reactivity with virus specific antibody in radioimmunoprecipitation tests showing production of the two different glycosylated conformational forms of GI and GII. The vaccinia promoter $P_{11}$ in the RCN recombinants regulated higher levels of G expression than $P_{7.5}$. These promoters functioned apparently the same as in earlier vaccinia virus: G recombinants.

Six different animal species were vaccinated according to the invention via the oral route. These species responded in varying degrees in producing rabies virus neutralizing antibodies (Nt. Abs). The results are reported in Tables 1 through 3 in the Examples below. Raccoons (*Procyon lotor*), a major reservoir animal for rabies in the United States, were fully protected against rabies virus challenge, suggesting that RCN recombinants can be used in the formulation of an oral delivered preparation of vaccine, such as an oral bait that contains vectored virus. The induction of rabies virus Nt. Abs. in 5 of 5 dogs and 1 of 3 skunks via the oral route of vaccination indicates that RCN recombinant vaccines appears to have unique and novel properties versus similar vaccinia virus based vaccines which have not yet proven to be as effective in these animal species. Protection of mice by footpad inoculation of either RCN recombinant suggests that injectable vaccines comprising immunogenic amounts of recombinant virus of the present invention in a pharmaceutically acceptable carrier, such as nontoxic buffers and the like, is now made possible. An earlier report indicated that RCN virus may be indigenous in nature, a unique property not known to be shared by vaccinia virus, which is generally considered as smallpox vaccine virus or virus propagated in laboratories. Of course, further studies on the host range, relative pathogenicity, current distribution of RCN virus in nature, together with regulatory scrutiny of such recombinants should be made before actual field trials of such vaccine. Diagnostic kits or other immune-reagents based on the current invention are also now made possible.

EXAMPLES

In the Examples below, the procedures to produce the recombinants and the vaccines were as described above. As previously described by Esposito et al., Virus Genes 1987:1:7–21, each of 6 NYBH vaccinia rabies-G recombinants induced rabies virus Nt. Abs. and protected mice when given by intradermal scarification or by footpad injection. One NYBH vaccinia: rabies-G recombinant preparation injected intramuscularly into 5 dogs protected them against rabies challenge. Furthermore, when 2 groups of 10 each of outbred mice were separately syringe-fed either of 2 of the 6 NYBH recombinant preparations, about 20% protection was noted; the mice survived challenge only when rabies virus Nt. Abs. were present in the serum. Moreover, feeding one recombinant NYBH virus preparation to 5 dogs induced no Nt. Abs. and was not protective. The efficacy of the present invention is demonstrated for each of the two RCN rabies-G recombinants that were tested by injecting or feeding them to mice, raccoons, or other animals.

EXAMPLE 1

Six-week-old colony-bred white, International Cancer Research (ICR) strain mice were separately fed the RCN recombinants by syringe at a dose of 30 ul containing $10^8$ or $10^9$ PFUs per mouse. The results of this example together with the results of administering recombinants by footpad inoculation are presented in Table 1.

TABLE 1

Protection Against Street Rabies of Mice Immunized with Raccoon poxvirus: Rabies virus Glycoprotein Recombinants

| Virus | Route: PFU dose/mouse | Mortality |
|---|---|---|
| RCN-GS62-JE-I | Footpad: | |
| | $10^9$ | 0/9 |
| | $10^8$ | 0/12 |
| | Oral: | |
| | $10^9$ | 5/11 |
| | $10^8$ | 9/12 |
| RCN-KB3-JE-13 | Footpad: | |
| | $10^9$ | 0/9 |
| | $10^8$ | 0/12 |
| | Oral: | |
| | $10^9$ | 1/10 |
| | $10^8$ | 7/12 |

Note: Raccoon poxvirus (RCN) recombinants RCN-GS62-JE-I or RCN-KB3-Je-13 at the indicated plaque-forming units (PEU per 30 ul) per mouse (colony-bred ICR mice) were separately syringe-fed or injected in one rear footpad. At 4 weeks post vaccination a few animals were tested for rabies virus neutralizing antibodies (Nt. Abs - International Units/ml of serum) by the Rapid Immunofluorescent Focus Inhibition Test (Smith, J.S. et al., WHQ Monogr. Ser. 1973:23:354–357). Then, one month after vaccination, the animals were challenged by footpad inoculation of about 1 $LD_{50}$ of Mexico dog street rabies virus. Rabies deaths 1 month postchallenge are shown.

Every attempt was made to deposit the vaccine dose directly by syringe into the mouth, only 23 of 45 mice orally vaccinated were protected against a challenge with street rabies virus. Two of 8 serum samples drawn before challenge of the mice showed Nt. Abs., which suggested that the 50% protection observed can be explained if inadvertant intranasal infection of these outbred mice was the reason for induction of the Nt. Abs. Alternatively, direct ingestion may have failed to produce uniform infection of the digestive tract or some degree of natural resistance to oral infection may exist in ICR mice. In contrast, 42 mice (100%) resisted street rabies virus challenge as shown in Table 1 after vaccination via footpad inoculation with either of the RCN recombinants which is similar to reported results with NYBH vaccinia: rabies-G recombinants. Prechallenge screening of sera from 9 of the 42 mice of this group showed that all 9 had developed high titers of rabies virus Nt. Abs. Taken together, the 2 positive sera from oral vaccinated mice in Table I and the 9 positive sera from the footpad vaccinated mice showed high titers of rabies Nt. Abs., (range per ml serum=4.5–10 International United (I.U.). No malaise, generalized dermal lesions, loss of appetite, or abnormal excretions were apparent during monitoring of mice vaccinated by either route of inoculation. The difficulty of uniformly infecting mice by feeding may be an advantageous property of RCN recombinants in a field trial of oral-bait vaccines, where potential for sustained transmission of RCN recombinants among and between animal species may be undesirable.

EXAMPLE 2

Initially, for this example, one raccoon was syringe-fed $10^{8.5}$ PFUs of RCN-GS62-JE-I virus. At one week postvaccination the raccoon showed significant rabies virus Nt. Abs. of 3.5 I.U./ml serum, rapidly rising to 80 I.U./ml by 2 weeks, then gradually leveling at 20 I.U./ml by 6 months. Groups of raccoons were then fed tallow-coated polyurethane sponge-baits (3 cm³) that contained (in phosphate-buffered saline with 20% fetal bovine serum (PBS-20FBS)) about $10^9$ PFU of the RCN: rabies-G recombinant viruses or of standard RCN virus. No apparent pathologic abnormalities of any kind were noted during daily monitoring of the vaccinated raccoons. High titers of rabies virus Nt. Abs. developed by 4 weeks' postvaccination in the animals fed the recombinants, and all of the recombinant vaccinated raccoons survived challenge with a street strain of raccoon rabies virus. These results are in Table 2.

TABLE 2

Antibodies and Protection Against Rabies of Raccoons Immunized with Raccoon poxvirus: Rabies virus Glycoprotein Recombinants

| Vaccine virus | Animal No. | Rabies virus Nt. Abs. | HI antibodies RCN | HI antibodies VAC | Post-challenge rabies death |
|---|---|---|---|---|---|
| RCN-GS62-JE-I | 29 | 20.3 | 80 | 80 | — |
| | 30 | 50.0 | 160 | 80 | — |
| | 31 | 50.0 | 80 | 80 | — |
| | 32 | >100 | 80 | 40 | — |
| | 33 | >100 | 320 | 80 | — |
| RCN-KB3-JE-13 | 24 | 45.0 | 160 | 160 | — |
| | 25 | 48.5 | 320 | 80 | — |
| | 26 | >100 | 320 | 160 | — |
| | 27 | 42.9 | 80 | 20 | — |
| | 28 | 40.7 | 160 | 40 | — |
| RCN | 17 | <5 | 640 | 160 | + |
| | 35 | <5 | 160 | 320 | — |
| | 36 | <5 | 320 | 80 | + |
| | 37 | <5 | 320 | 160 | + |

Note: Raccoon poxvirus (RCN) recombinants RCN-GS62-JE-I, RCN-KB3-JE-13, and standard RCN were fed separately to colony bred raccoons. One tallow-coated polyurethane sponge-bait (3 cm³) filled with $10^9$ PFUs of virus in PBS was placed in each cage after food was withheld from the animals for 24 hr. Animals were tested for rabies virus neutralizing antibodies (Nt. Abs.-=International Units/ml of serum) by the Rapid Immunofluorescent Focus Inhibition Test (Smith, J.S. et al., WHO Monogr. Ser. 1973:23:354–357), and for RCN or vaccinia (VAC) virus hemagglutination inhibiting (HI) antibodies (reciprocal end-point dilution of serum) (Thomas, E.K. et al., Arch. Virol. 49:217–227). Animals showed no prevaccinal HI or Nt. Abs.; titers at 4 weeks' postvaccination are shown. Two months after vaccination the animals were challenged by bilateral masseter inoculation of a previously determined lethal dose ($\geq 5$ $LD_{50}$) of street rabies virus that had been isolated from a raccoon in Virginia. Rabies deaths by 6 months' postchallenge are shown.

The results of this example also demonstrate that all the raccoons developed similar hemagglutination-inhibiting (HI)antibody levels to a RCN virus hemagglutinin (HA) or vaccinia virus HA preparation (Table 2). These data suggested that the HI test may be useful for sero-surveys to determine current distribution of RCN virus in wildlife.

EXAMPLES 3 THROUGH 6

In further efficacy experiments on host-range, and pathogenetic and immunologic responsiveness of various animal species, recombinant RCN-KB3-JE-13 virus was syringe-fed to cotton rats, rabbits, dogs, and striped skunks. The results of these examples are in Table 3.

TABLE 3

Rabies virus-neutralizing antibodies in four animal species vaccinated by syringe-feeding raccoon poxvirus: rabies-G recombinant RCN-KB3-JE-13

| Experiment 3 | | Experiment 4 Skunk | | Experiment 5 Rabbit | | Experiment 6 Cotton | |
|---|---|---|---|---|---|---|---|
| Dog No. | Ab | No. | Ab | No. | Ab | Rat No. | Ab |
| 327 | 1.4 | 85-1 | 0.0 | 1 | 0.0 | 1 | >4.5 |
| 90 | 0.4 | 85-4 | 0.0 | 2 | >4.5 | 2 | >4.5 |
| 32 | 1.8 | 85-5 | 1.8 | 3 | 0.0 | 4 | >4.5 |
| 39 | 0.1 | | | 4 | >4.5 | 5 | >4.5 |
| 4 | 0.4 | | | 5 | >4.5 | 7 | 4.5 |
| | | | | 6 | 0.9 | 8 | >4.5 |
| | | | | | | 10 | 0.4 |
| | | | | | | 11 | 0.0 |
| Mean Titer: | 0.8 | | 0.6 | | >2.4 | | >3.4 |

Note: Rabies virus-neutralizing antibody (Ab) titers are International Units per ml serum. Serum samples were from blood drawn at 4 weeks' postvaccination except for cotton rats which were test-bled at two weeks' postvaccination. Recombinant RCN-KB3-JE-13 virus was syringe-fed as follows: dogs received 2 ml containing $10^{8.3}$ PFUs, striped skunks received 0.5 ml containing $10^{7.6}$ PFUs, rabbits received 0.5 ml containing $10^{7.6}$ PFUs, cotton rats received 0.1 ml containing $10^{7.1}$ PFUs.

At the doses used (Table 3) most of the cotton rats (2 weeks' postvaccination (wpv)) and rabbits (4 wpv) showed relatively rapid production of significant levels of rabies virus Nt. Abs. (titer range for 6 rabbits 0–4.5 I.U./ml serum, for 8 cotton rats=0–4.5 I.U./ml); 1 of 3 skunks, each fed $5 \times 10^{7.1}$ PFUs, showed moderate Nt. Abs. (1.8 I.U./ml). In contrast to the lack of induction of Nt. Abs. when a NYBH vaccinia: G recombinant was fed to dogs, $2 \times 10^{8.1}$ PFUs of RCN-KB3-JE-13 fed to each of 5 dogs induced moderate titers in each animal within 4 wpv (range=0.1–1.4 I.U./ml). Standard and recombinant RCN virus infection appeared innocuous for the 6 animal species vaccinated to date. At 6 months post vaccination, all recombinant vaccinated cotton rats survivied an otherwise lethal challenge by footpad injection of rabies street virus. More dose-response determinations and rabies challenges of these and other animals species are in progress.

What is claimed is

1. A recombinant virus having all of the characteristics of ATCC deposit number VR 2212.

2. A vaccine for rabies, comprising:
   a pharmaceutical excipient; and
   a therapeutically effective amount of a recombinant raccoon poxvirus, said raccoon poxvirus being a host organism that contains a nucleotide sequence encoding a rabies virus glycoprotein G gene expressed via a vaccinia virus promoter.

3. A method for inducing protective immunity against rabies comprising:
   administering to a host, said host being susceptible to rabies, an immunogenic amount of a vaccine for rabies, said vaccine having a recombinant raccoon poxvirus, said raccoon poxvirus being a host organism that contains a nucleotide sequence encoding a rabies virus glycoprotein G, wherein said rabies virus glycoprotein G is expressed via a vaccinia virus promoter.

4. The method of claim 3 wherein said administering of said vaccine is by oral baiting.

5. A recombinant virus comprising:
   raccoon poxvirus host organism;
   a nucleotide coding sequence for rabies virus glycoprotein; and
   a vaccinia virus promoter which drives expression of said nucleotide coding sequence.

6. The virus of claim 5, wherein said promoter is a vaccinia late promoter.

7. The virus of claim 6, wherein said promoter is a $P_{11}$ or $P_{7.5}$ promoter.

8. A method for making a vaccine comprising a recombinant raccoon poxvirus, which comprises:
   providing a raccoon poxviral DNA having a vaccinia virus late promoter, and
   inserting into said raccoon poxviral DNA a nucleotide sequence which encodes a rabies virus glycoprotein G, wherein said nucleotide sequence is linked to said vaccinia virus late promoter so as to be expressed under the control of said promoter.

9. The method of claim 8 wherein said nucleotide sequence is inserted in the thymidine kinase gene of the raccoon pox viral DNA.

10. The method of claim 8, wherein said late promoter is a $P_{11}$ or $P_{7.5}$ promoter.

* * * * *